(12) United States Patent
Bovenkamp

(10) Patent No.: US 9,084,659 B2
(45) Date of Patent: Jul. 21, 2015

(54) FLEXIBLE DRIVE SHAFT FOR AN ECCENTRIC WEIGHT-DRIVEN PERSONAL CARE APPLIANCE

(75) Inventor: Marc Darrin Bovenkamp, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 264 days.

(21) Appl. No.: 13/812,896

(22) PCT Filed: Aug. 1, 2011

(86) PCT No.: PCT/IB2011/053413
§ 371 (c)(1),
(2), (4) Date: Jan. 29, 2013

(87) PCT Pub. No.: WO2012/020351
PCT Pub. Date: Feb. 16, 2012

(65) Prior Publication Data
US 2013/0125320 A1     May 23, 2013

Related U.S. Application Data

(60) Provisional application No. 61/371,762, filed on Aug. 9, 2010.

(51) Int. Cl.
*A61C 17/34* (2006.01)
*A61C 17/16* (2006.01)
*F16H 23/00* (2006.01)

(52) U.S. Cl.
CPC ............. *A61C 17/16* (2013.01); *A61C 17/3481* (2013.01); *F16H 23/00* (2013.01); *Y10T 74/18344* (2015.01)

(58) Field of Classification Search
CPC .................. A61C 17/3481; A61C 17/3409
USPC ............ 15/22.1, 22.2, 22.4, 28; 74/61, 70, 82, 74/86–87; 464/87–88, 97, 100, 51, 52
See application file for complete search history.

(56) References Cited

U.S. PATENT DOCUMENTS 8,695,143 B2 * 4/2014 Kloster ........................ 15/22.1
8,793,829 B2 * 8/2014 Shimoyama et al. .......... 15/22.1
(Continued)

FOREIGN PATENT DOCUMENTS

WO     2005067764 A1    7/2005
WO     2006004316 A1    1/2006
(Continued)

OTHER PUBLICATIONS

G.J. Matthews et al, "Calculation of Stress-Concentration Factors for Grooved Shafts in Bending Using the Point-Matching Technique", The Journal of Strain Analysis for Engineering Design, 1973, vol. 8 (2), pp. 113-118.

*Primary Examiner* — Laura C Guidotti

(57) ABSTRACT

The appliance includes a DC motor (12) having a rotating output shaft (14). A flexible coupling member (22) is connected at one end to the output shaft, and at the other end is connected to an eccentric mass (24). The end of the coupling member with the eccentric mass is connected to a V-spring assembly (16) which drives a workpiece assembly (18) on a distal end of which is mounted a workpiece (19). The spring assembly constrains the rotational movement of the coupling member to produce an oscillating, back-and-forth action of the workpiece shaft and the workpiece through a desired angle. The coupling member is elongated, and is elliptical in cross-section in an active region (34), having a thin dimension (38) in the direction in which the active portion bends during operation of the motor and rotation of the motor output shaft.

15 Claims, 5 Drawing Sheets

(56) References Cited

U.S. PATENT DOCUMENTS

| | | | |
|---|---|---|---|
| 8,863,344 B2* | 10/2014 | Kloster | 15/22.2 |
| 2003/0079304 A1* | 5/2003 | Dworzan | 15/22.1 |
| 2009/0320221 A1* | 12/2009 | Masuko | 15/22.1 |
| 2010/0251493 A1* | 10/2010 | Sale et al. | 15/22.1 |
| 2012/0036658 A1* | 2/2012 | Schaefer et al. | 15/28 |

FOREIGN PATENT DOCUMENTS

| | | |
|---|---|---|
| WO | 2008026383 A1 | 3/2008 |
| WO | 2011058466 A1 | 5/2011 |

* cited by examiner

FLEXIBLE DRIVE SHAFT FOR AN ECCENTRIC WEIGHT-DRIVEN PERSONAL CARE APPLIANCE

This invention relates generally to a personal care appliance, such as a toothbrush, and more specifically concerns a particular drive assembly for the appliance, using an eccentric mass.

One way to drive a workpiece in a personal care appliance is through the use of a flexible drive shaft responsive to the action of a DC drive motor, wherein the flexible drive shaft, also referred to as a coupling member, has an eccentric mass on the distal end thereof. The flexible coupling member with the eccentric is used to drive a spring mass assembly which in turn produces a selected movement of a workpiece such as a brushhead. The flexible coupling member is typically elongated and round in cross-section. The coupling member in operation of the appliance experiences both bending and torque stresses as it bends due to the rotation of the drive motor, transferring the torque from the drive motor to the spring mass assembly.

With conventional, round cross-sectional coupling members, however, substantial bending stresses are experienced in the vicinity of the ends of the coupling member adjacent the attachment elements for the motor drive shaft at one end and to the eccentric assembly at the other end. This concentration of stress significantly reduces the life of the coupling member. One attempt to increase the life of coupling members involved increasing the length of the coupling member so as to maintain the bending stresses at a lower level to avoid failure. However, this results in increasing the length of the appliance, which in many commercial applications is undesirable.

Hence, it is desirable to have a coupling member for a personal care appliance, which includes an eccentric, which can tolerate the bending stress levels in operation of the appliance for a reasonable life, while at the same time resulting in an appliance length within desirable commercial limits.

Accordingly, the personal care appliance comprises: a DC motor having an output shaft which rotates; a flexible coupling member connected to the drive shaft at a proximal end thereof and having an eccentric mass mounted at a distal end thereof a workpiece assembly including a workpiece at a distal end thereof; and a spring hub assembly driven by the coupling member and eccentric mass, which constrains the rotational movement of the coupling member to an oscillating action of the workpiece shaft assembly, wherein the coupling member is elliptical in cross-section in an active region thereof, having a thin dimension and a wider dimension, with the thin dimension in the direction of the bending of the coupling member during operation of the appliance and the wider dimension perpendicular thereto.

Figure 1:
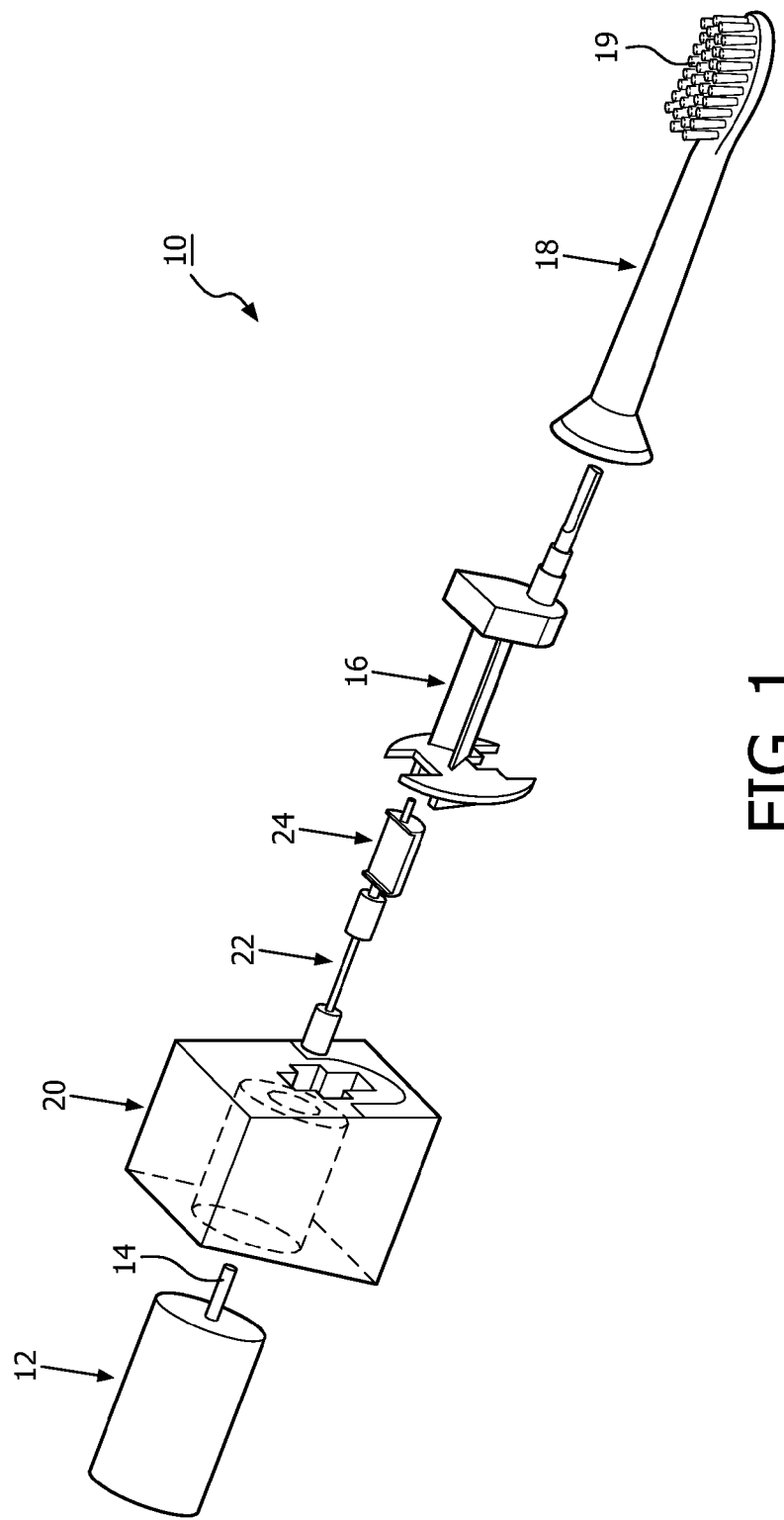
FIG. 1 is a perspective, exploded view of the major structural portions of a personal care appliance, in particular, a power toothbrush, which includes the coupling member disclosed herein.

FIG. 1 shows the principal structural elements of a personal care appliance, in particular a power toothbrush. It should be understood, however, that the appliance could be a different personal care appliance, such as an electric shaver, a massager, a scrubber or the like. The use of a power toothbrush appliance is for clarity of illustration and because it is anticipated to be a primary use for the flexible drive shaft with eccentric arrangement disclosed herein.

The appliance, shown generally at 10, includes a DC motor 12 having an output shaft 14 which rotates at a selected frequency, which depends upon the particular appliance. In this arrangement for a power toothbrush application, a suitable frequency is 250 Hz, although this can be varied, over a large range. In general operation of the appliance of FIG. 1, the rotation of the output shaft of motor 12 is used to drive a V-spring and brush hub assembly, referred to generally at 16, which results in a sweeping, i.e. oscillating, motion of a brushhead assembly 18, which includes a brush member workpiece 19, for cleansing of a user's teeth.

Motor 12 is contained in a motor mount assembly 20 which is positioned within an appliance body (not shown). Extending between output shaft 14 of the motor and the V-spring brush hub assembly 16 is a flexible coupling member 22 with an eccentric mass 24 on the distal end thereof, adjacent the V-spring/brush hub assembly 16. In proper operation, eccentric mass 24 must rotate at a fast enough rate to utilize the inertia of the eccentric to produce the desired oscillatory action of the brushhead assembly 18. The V-spring/brush hub assembly 16 constrains the movement of the brushhead assembly to the desired oscillatory action through a selected angle relative to the rotating action of the eccentric.

The rotation of the eccentric 24 requires that the coupling member 22 on which the eccentric is mounted be flexible, because motor 12 is stationary within the motor mount while the V-spring assembly and the brushhead assembly and brush member move.

Figure 2:
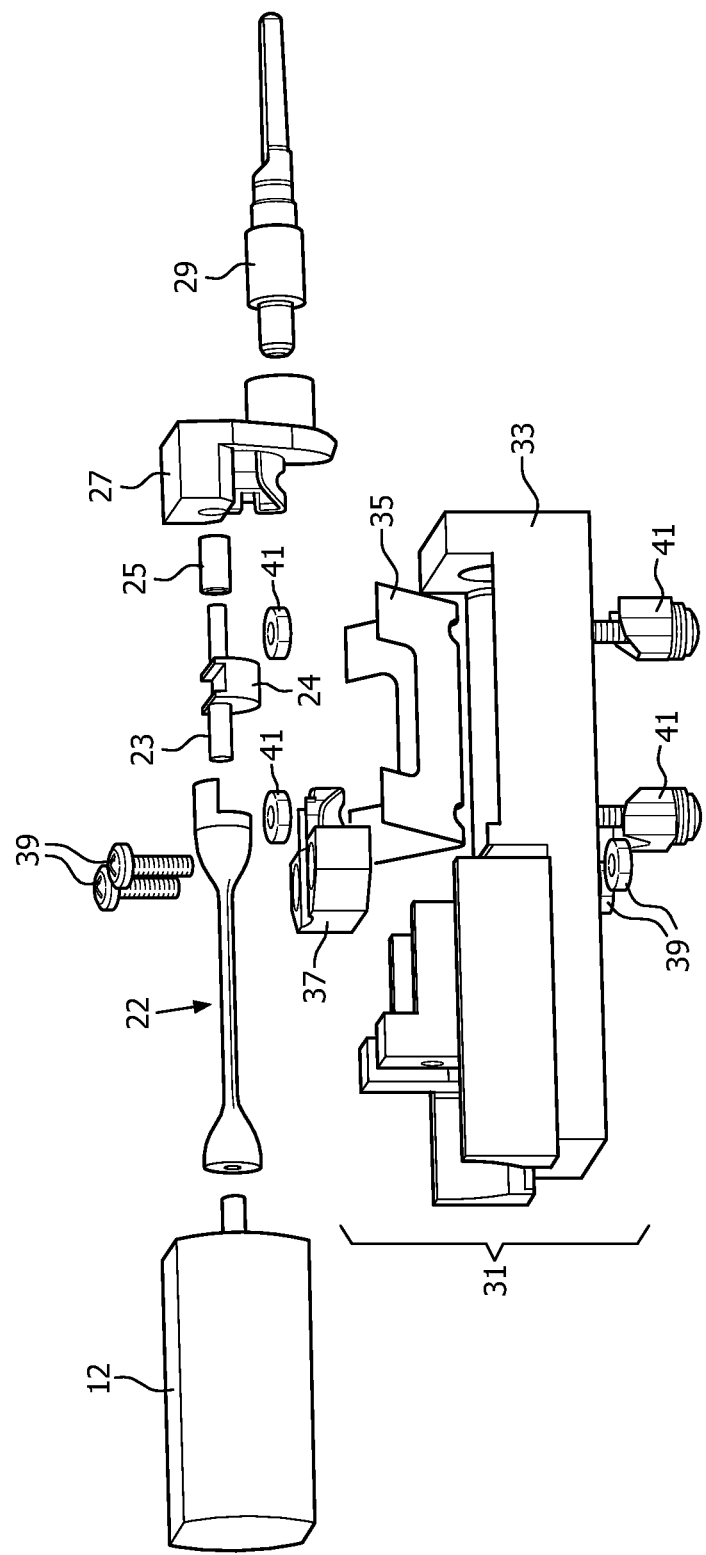
FIG. 2 is a more detailed exploded view of the appliance of FIG. 1.

FIG. 2 shows a more detailed exploded view of the appliance of FIG. 1. It includes motor 12 and coupling member 22. The distal end of coupling member 22 fits on to an eccentric mass 24 which includes a shaft 23. On the outer end of shaft 23 is a bushing 25, which fits into a brushhead hub member 27. Brushhead hub member 27 drives a brushhead assembly shaft 29, on which is mounted brushhead assembly 18. A V-spring assembly 31 is shown exploded away in FIG. 2, including a spring frame 33, a V-shaped spring 35 and a spring mount 37 which secures the V-spring to the frame by means of two bolt/nut combinations 39. Also securing the V-spring to the spring mount and to the brushhead hub member 37 are two V-block/nut combinations 41. A similar V-spring arrangement with an eccentric drive train is also shown in co-pending provisional application Ser. No. 61/261,402, owned by the assignee of the present invention. The contents of that application are hereby incorporated by reference herein.

In this arrangement, coupling member 22 in operation will always bend in the same direction, i.e. the same plane. It will bend back and forth, between a no-bend condition and an "S" shape, in one direction (plane) only. Typically, and in the present arrangement, coupling member 22 bends in such a way that the higher stresses on the article are in line with the location of the highest moment of inertia of the spinning eccentric mass. In more detail, coupling member 22 includes connecting portions 30 and 32 which connect, respectively, to the drive shaft from the motor and to the eccentric at the opposing end of the coupling member. Intermediate of the connecting portions 30 and 32 is an elongated active intermediate portion 34.

Figure 3:
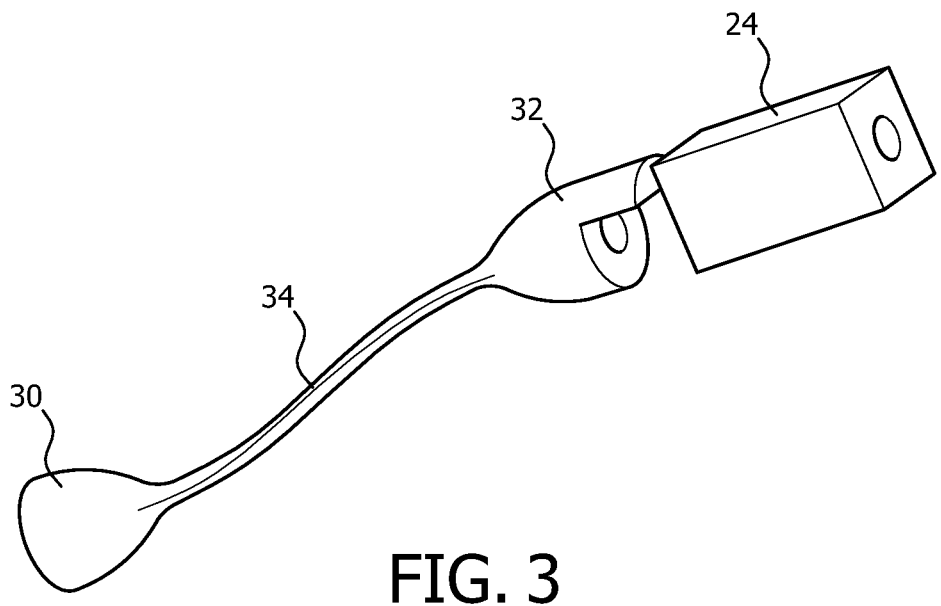
FIG. 3 is one perspective view of the coupling member disclosed herein and shown in FIG. 1.

FIGS. 2 and 3 show most clearly connecting portions 30 and 32 and the active portion 34 of the coupling member and their relationship. The connecting portions 30, 32, also referred to as transition portions, are quite short so that they do not significantly reduce the length of the active portion. Typically, the transition portions will be large enough to encompass the motor drive shaft 14 on the one end and the eccentric mass shaft on the other end, so that there are no overly stressed portions of coupling member 22 due to the shafts inserted in each connection portion 30, 32. Eccentric 24 is shown representationally in FIG. 3 without shaft portions extending from either end, as shown in FIG. 2.

The eccentric 24 on the end of the coupling member creates bending stresses which are related to the actual eccentricity of the eccentric. In one embodiment, the mass is 0.845 grams and the distance between the axis of the eccentric and the axis of the motor shaft is approximately 2 mm.

Figure 4:
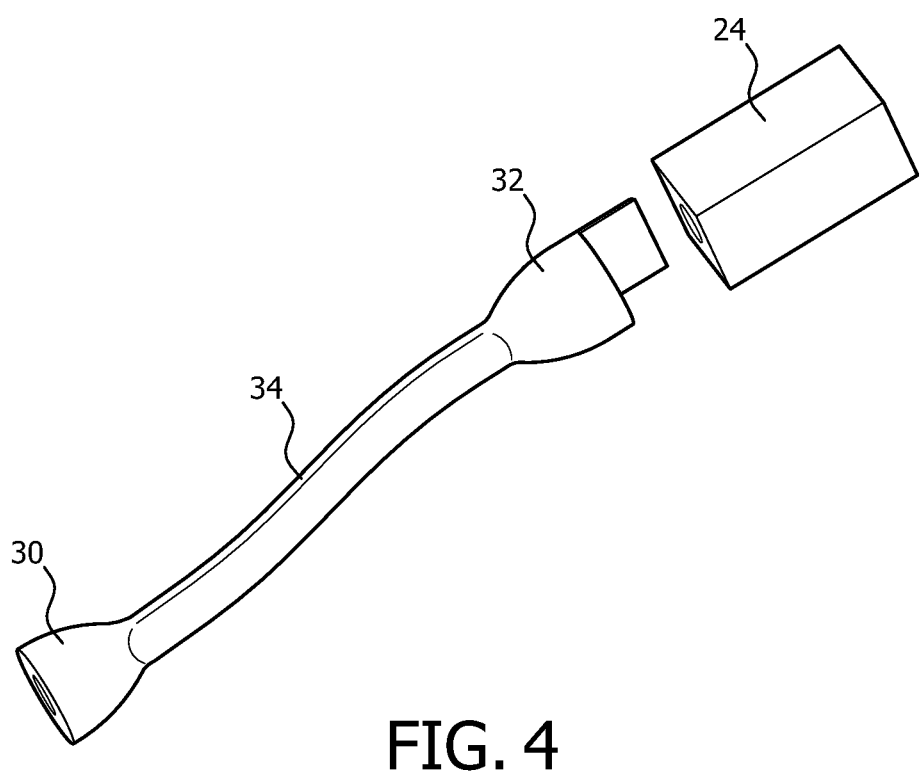
FIG. 4 is another perspective view of the coupling member of FIGS. 1 and 2.
Figure 5:
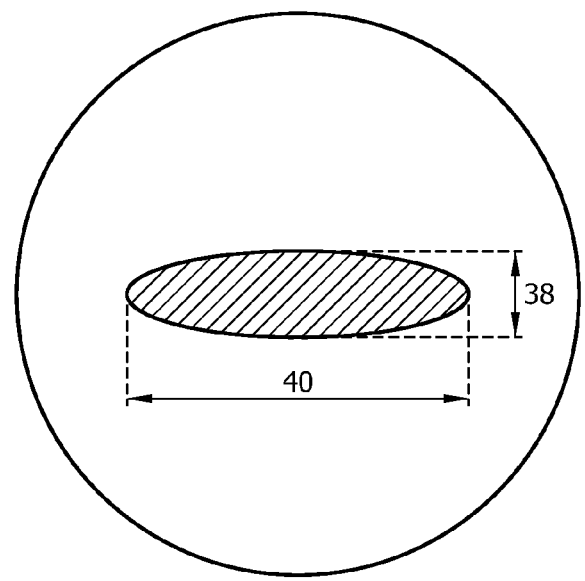
FIG. 5 is a cross-sectional view of the coupling member of FIGS. 1-3.

Referring to FIGS. 3, 4 and 5, in order to reduce the resulting bending stress on the coupling member, particularly the ends of the active portion at the connection portions, the height (cross-sectional dimension 38) of active portion 34 of the coupling member is reduced in the direction of the bending of the coupling member, while the width (cross-sectional dimension 40) of the coupling member perpendicular to the direction of bending is increased to retain the required torque load transfer/carrying capability. This results in the active portion 34 having an elliptical cross-section between the connecting portions 30, 32. The result of this arrangement is a reduction in the bending stress on the coupling member, in particular at the two ends of the active portion, thereby significantly increasing the life of the coupling member, without negatively affecting the torque transfer capability between the motor and the V-spring hub assembly. The coupling member is thus optimized to accommodate both the bending and torque stress load, while providing the required torque transfer capability to maintain efficiency and proper operation of the appliance.

In one embodiment, the thickness of the active portion in the bending direction 38 will be approximately 0.75 mm, while in the perpendicular (non-bending) direction 40, the thickness of the active portion will be 4.5-5 mm. While the above dimensions are preferred, it should be understood that other particular dimensions can be used.

Figure 6:
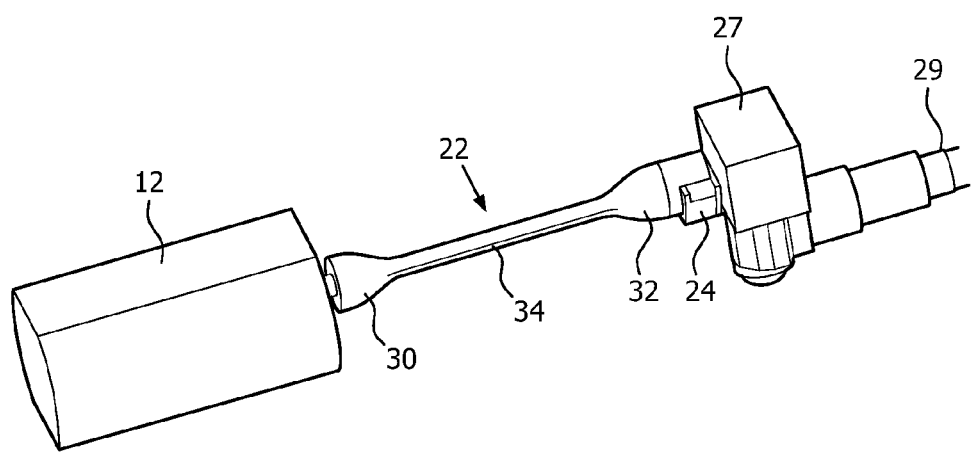
FIG. 6 is a perspective view of the coupling member at a 0° rotation.
Figure 7:
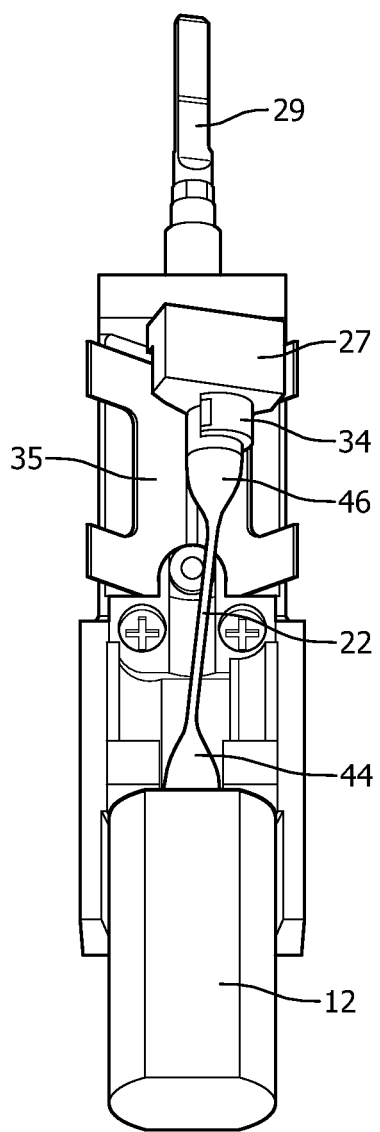
FIG. 7 is a top view of the coupling member at a 90° rotation.
Figure 8:
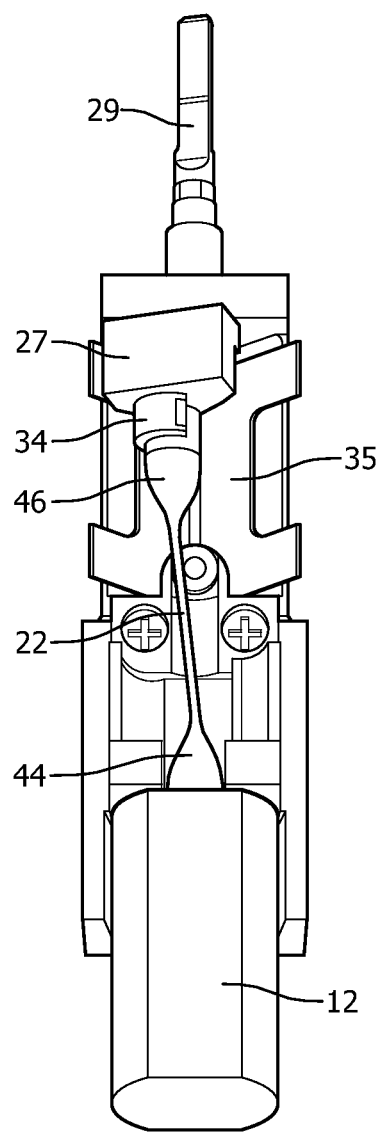
FIG. 8 is a top view of the coupling member at a 270° rotation.

FIGS. 6, 7 and 8 show the operation of the drive assembly during one rotation of the motor. At 0° (FIG. 6), the coupling member 22 will be straight from end to end with no bending. At 90° (FIG. 7), the proximal end 44 will rotate, and the distal end 46 will bend away from the axial center line of the motor shaft, which is the proximal end of the coupling member. At 180° rotation of the motor shaft, the coupling member will be again in a non-bent, straight configuration. At 270°, shown in FIG. 8, the coupling member will bend in the opposite direction from that of FIG. 7. In the embodiment shown, the distance between the center line of the motor and the coupling member at its proximal end relative to the center line of the distal end of the coupling motor at its maximum displacement at 90° and 270° will be approximately 2 mm, in each direction. This distance can, of course, change with different arrangements of the coupling member. This arrangement, as noted above, results in an oscillating action of the brushhead shaft and the workpiece, over an angle in the range of 11°-13° in the particular embodiment shown but can be a larger angle.

Accordingly, the drive train can be made a desirable length while still permitting the required eccentric motion for desired workpiece action. The drive shaft with eccentric configuration disclosed herein results in both a longer life for the coupling member, desired workpiece action, and a favored appliance length.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A personal care appliance, comprising:
a DC motor having an output shaft which rotates;
a flexible coupling member connected to the output shaft at a proximal end thereof and having an eccentric mass mounted at a distal end thereof, wherein the flexible coupling member is capable of bending;
a workpiece assembly including a workpiece at a distal end thereof; and
a spring hub assembly driven by the coupling member and eccentric mass, which constrains the rotational movement of the coupling member to an oscillating action of the workpiece assembly, wherein the coupling member is elliptical in cross-section in an active region thereof, wherein the active portion is elliptical in configuration along the entire length thereof, having a thin dimension and a wider dimension with the thin dimension in the direction of the bending of the coupling member during operation of the appliance and the wider dimension perpendicular thereto.

2. The appliance of claim 1, wherein the appliance is a power toothbrush.

3. The appliance of claim 1, wherein the frequency of the DC motor is approximately 250 Hz.

4. The appliance of claim 1, wherein the flexible coupling member is a plastic material.

5. The appliance of claim 1, wherein the eccentric has a mass of approximately 0.845 grams and a distance of approximately 2 mm from a center line of the motor output shaft.

6. The appliance of claim 1, wherein the elliptical configuration of the coupling member is substantially the same over the entire active region.

7. The appliance of claim 1, wherein the coupling member is approximately 0.75 mm in one dimension and approximately 4.5-5 mm in a perpendicular dimension to the one dimension.

8. A personal care appliance, comprising:
a DC motor having an output shaft which rotates;
a flexible coupling member connected to the output shaft at a proximal end thereof and having an eccentric mass mounted at a distal end thereof, wherein the flexible coupling member is capable of bending;
a workpiece assembly including a workpiece at a distal end thereof; and
a spring hub assembly driven by the coupling member and eccentric mass, which constrains the rotational movement of the coupling member to an oscillating action of the workpiece assembly,
wherein the coupling member is elliptical in cross-section in an active region thereof, having a thin dimension and a wider dimension with the thin dimension in the direction of the bending of the coupling member during operation of the appliance and the wider dimension perpendicular thereto, and
wherein the coupling member includes two connecting portions at opposing ends thereof for connecting to the output shaft of the DC motor and to the eccentric mass, respectively, and an active region intermediate of the two connecting portions, and wherein the active portion is elliptical in configuration along the entire length thereof.

9. The appliance of claim 8, wherein the elliptical configuration of the coupling member is substantially the same over the entire active region.

10. The appliance of claim 8, wherein the connecting portions are long enough, respectively, to encompass a substantial portion of the motor output shaft at the end of the coupling member and a portion of the eccentric mass shaft at the other end.

11. The appliance of claim 8, wherein the coupling member is approximately 0.75 mm in one dimension and approximately 4.5-5 mm in a perpendicular dimension to the one dimension.

12. The appliance of claim 8, wherein the appliance is a power toothbrush.

13. The appliance of claim 8, wherein the frequency of the DC motor is approximately 250 Hz.

14. The appliance of claim 8, wherein the flexible coupling member is a plastic material.

15. The appliance of claim 8, wherein the eccentric has a mass of approximately 0.845 grams and a distance of approximately 2 mm from a center line of the motor output shaft.

* * * * *